United States Patent [19]
Bohning

[11] Patent Number: 6,084,163
[45] Date of Patent: Jul. 4, 2000

[54] INBRED CORN LINE BE4547

[75] Inventor: Kermit Bohning, Belmond, Iowa

[73] Assignee: Cargill Incorporated, Wayzata, Minn.

[21] Appl. No.: 09/289,051

[22] Filed: Apr. 9, 1999

[51] Int. Cl.[7] ............................... A01H 5/00; A01H 5/10; A01H 1/04; C12N 5/04
[52] U.S. Cl. ...................... 800/320.1; 800/298; 800/275; 435/412; 435/424; 435/430; 435/430.1
[58] Field of Search .................. 800/320.1, 275, 800/298, 271; 435/412, 424, 430, 430.1

[56] References Cited

U.S. PATENT DOCUMENTS

| | | | |
|---|---|---|---|
| 4,581,847 | 4/1986 | Hibberd et al. | 47/58 |
| 5,484,956 | 1/1996 | Lundquist et al. | 800/205 |

OTHER PUBLICATIONS

Kamo et al., "Establishment and Characterization of Long-–Term Embryogenic Maize Callus and Cell Suspension Cultures", *Plant Science*, 1986, 45:111–117.

Vasil et al., "Plant Regeneration from Friable Embryogenic Callus and Cell Suspension Culture of *Zea mays* L.", *J. Plant Physiol.*, 1986, 124:399–408.

Phillips et al. "Cell/Tissue Culture and In Vitro Manipulation", In Corn and Corn Improvement, 3rd. Ed., ASA Publication, #18, pp. 345–349 & 356–357, 1988.

*Primary Examiner*—Gary Benzion
*Assistant Examiner*—Melissa L. Kimball
*Attorney, Agent, or Firm*—Fish & Richardson, P.C.

[57] ABSTRACT

Inbred corn seed designated BE4547 and corn plants produced from that seed are disclosed. The invention includes plant parts from BE4547 corn plants. The invention includes a corn plant displaying all the physiological and morphological characteristics of a BE4547 corn plant, BE 4547 pollen grains, plant parts, and tissue cultures. The invention also provides hybrid corn seed produced by crossing a BE4547 inbred corn plant with a second inbred corn plant.

7 Claims, No Drawings

INBRED CORN LINE BE4547

FIELD OF THE INVENTION

The invention relates to genetics, plant physiology, agronomy, corn breeding and inbred corn lines.

BACKGROUND OF THE INVENTION

Corn (*Zea mays* L.) is a monoecious plant, i.e., the male and female flowers develop on the same plant. They are located on the tassel and ear, respectively. Each silk on the ear represents an individual female flower, and each kernel represents a separate pollination event. Natural pollination occurs when pollen falls from the tassel onto the silk of the same plant, or is carried by wind from the tassel of one plant to the silk of a neighboring plant.

Corn breeders have employed controlled pollination, artificial selection, and genetic analysis to develop numerous genetic lines or varieties of corn that display desired traits such as yield potential, maturity time, disease resistance, insect resistance, ear size, plant height, drought tolerance. Established lines have been used as starting material for further rounds of crossing, selection, and analysis, to develop new and different varieties that display enhancement of particular traits or new combinations of traits.

The totality of the observable traits of a corn plant, i.e., the phenotype, results from the presence and interaction of many thousands of individual genetic loci. Each locus includes a pair of alleles, i.e., one from each parent. When a plant contains different alleles at a large number of loci, the plant is said to be heterozygous. In accordance with classical (Mendelian) genetics, a cross between two heterozygous plants yields a highly heterogenous (nonuniform) population of offspring. Thus, heterozygous plants are not "true-breeding." However, crosses of heterozygous plants are useful starting material for creation of new inbred, i.e., highly homozygous, lines, which are true-breeding.

Creation of a new inbred line can begin with selection of individual lines or populations judged superior with respect to one or more traits of interest. The genetic backgrounds of the selected plants are combined by crossing to create a gene pool upon which selection for desired traits may be practiced. Selected progeny plants are self-pollinated and plants in the next generation that exhibit the desired phenotype(s) are selected for further selfing. This process can be repeated for several generations (typically 5–8 generations designated $F_1$, $F_2$, $F_3$, etc.), until the desired degree of homozygosity is achieved.

Pedigree breeding and recurrent selection breeding are two methods that can be used to develop inbred lines from breeding populations. Pedigree breeding typically begins with the crossing of two different genotypes, and superior plants are selfed and selected in successive generations. In pedigree breeding, five or more generations of selfing and selection typically is practiced. Recurrent selection breeding can be used to improve an inbred line, e.g., to transfer a specific desirable trait from one germplasm source to an inbred that lacks the trait.

Inbred lines, however made, typically display relatively poor growth and vigor. Nevertheless, two (or more) different inbred lines can be crossed to produce a heterozygous hybrid that displays growth and vigor superior to that of either inbred parent line. This phenomenon is known as hybrid vigor or heterosis. Because of hybrid vigor, practically all corn produced in the United States is grown from hybrid seeds. In some cases, hybrid seeds are produced from controlled crosses of three or even four different inbred lines.

SUMMARY OF THE INVENTION

The present invention provides inbred corn seed designated BE4547 (ATCC accession number 203444), and corn plants produced from that seed (BE4547 plants). The invention includes plant parts from BE4547 corn plants. The invention includes a corn plant displaying all the physiological and morphological characteristics of a BE4547 corn plant. The invention provides pollen grains from BE4547 corn plants. The invention includes a tissue culture derived from a BE4547 corn plant or derived from a BE4547 plant part. In some embodiments of the invention, the tissue culture yields regenerated plants having the genotype of inbred line BE4547 or displaying all the physiological and morphological characteristics of a BE4547 corn plant. The invention also provides hybrid corn seed produced by crossing a BE4547 inbred corn plant with a second inbred corn plant.

The invention also provides an $F_1$ hybrid corn plant produced by planting and growing seeds of a first corn inbred line designated BE4547 in pollinating proximity to seeds of a second corn inbred line, preventing pollen production on plants resulting from either the first or said second inbred line seeds, allowing cross pollination to occur between the plants of the inbred lines, harvesting seeds produced on the plants in which pollen production was prevented, and growing at least one of the harvested seeds.

DEFINITIONS

As used herein, corn plant "parts" means cells, protoplasts, tissue cultures from which corn plants can be regenerated, calli, plant clumps, embryos, pollen, flowers, kernels, ears, cobs, leaves, husks, stalks, roots, root tips, anthers, silk and other intact organs or tissues of a corn plant.

Maturity—Silk (maturity time from planting to 50% of plants in silk) is measured in days and heat units (also called GDU=growing degree units).

Maturity—Pollen (maturity time from planting to 50% of plants in pollen) is measured in days and heat units.

10–90% Pollen Shed (maturity time from 10% pollen shed to 90% pollen shed) is measured in days and heat units.

Heat Unit (GDU; growing degree unit) is calculated according to the following formula:

GDU=[(daily max temp)+(daily min temp)]/2−50

The basis of the formula is the following. Temperatures within the range of 50–86° F. are considered adequate for maize growth. Temperatures outside this range are not conducive to growth and are given a value of 50 or 86, respectively, for purposes of GDU calculation. GDUs are calculated from planting date on a daily basis. Cumulative values to certain growth stages are calculated.

Plant Height is measured from the ground to the tip of the tassel, and is measured in centimeters (cm).

Ear Height is measured from the ground to the highest developed ear node attachment, in cm.

Length of Top Ear is a measure from the tip of the ear to the internode, and is measured in cm.

Ears is the average number of ears per plant.

Width Ear Node Leaf is the width of the leaf at the top ear node at its widest point, in cm.

No. Lvs Above Ear (number of leaves above the ear) is the number of leaves above the top ear node.

Degrees Leaf Angle is the adaxial angle between the stalk and the second leaf above the ear, at anthesis.

Leaf Sheath Pubesc (leaf sheath pubescence) is a visual measure of leaf hair density on the second leaf above the ear.

It is rated on a scale from 1 to 9, with 1 being no leaf hair, and 9 being comparable to peach fuzz.

Leaf Margin Waves is a visual measure of waviness at the edges of the leaves on the plant, and is measured on a scale of 1 to 9, with 1 being no waves, and 9 being many waves.

No. Prim. Lat. Branches (number of primary lateral branches on tassel) is the number of lateral tassel branches that originate from the central spike.

Branch Angle is the adaxial angle between the central spike and the second primary lateral tassel branch from the top, at anthesis.

Tassel Length is the length of the tassel from the top leaf collar to the tassel tip, and is measured in cm.

Pollen Shed is a visual measure of the amount of pollen shed by the tassel, and is rated on a scale of 1 to 9, with 1 being none (male sterile), and 9 being heavy shed.

Husk Tightness is measured on a scale of 1 to 9, with 1 being very loose, and 9 being very tight. This is measured at 65 days after 50% silking.

Ear Length is the length of the ear, from butt to tip, after husk removal, and is measured in cm.

Mid Point Diam (mid point diameter) is a measure of the diameter of the ear, including kernels, midway along the length of the ear, after husk removal. It is measured in millimeters (mm).

Ear Weight is a measure of ear weight after drydown and husk removal, and is measured in grams (gm).

Kernel Rows is the average total number of kernel rows on the ear. If the rows are indistinct, this value is the average number of kernels located around the circumference of the ear at the mid-point of its length.

Kernel Length is measured in mm.

Kernel Width is measured in mm.

Kernel Thickness is measured in mm.

% Round Kernels is the percentage of round kernels in an unsized sample, using a $^{13}\!/_{64}$" slot screen.

100 K Wt is the weight of 100 kernels taken from an unsized sample, and is measured in gm.

Mid Cob Diam (mid cob diameter) is a measure of the diameter of the cob midway along its length, after husk and kernel removal. It is measured in millimeters (mm).

% Dropped Ears is the percentage of plants whose ears have fallen to the ground at 65 days after anthesis.

% Root Lodging is the percentage of plants leaning at an angle greater than 30°, just before anthesis.

Yield Per Se is weight of kernels (measured at 12–13% grain moisture) per unit area of cultivated land, and is measured in kilograms per hectare (kg/ha).

NLB (northern leaf blight; *Exserohilum turcicum*) disease rating is scored visually on a scale of 1 to 9, with 9 indicating the highest disease resistance.

SLB (southern leaf blight; *Bipolar maydis*) disease rating is scored visually on a scale of 1 to 9, with 9 indicating the highest disease resistance.

NLS (northern leaf spot; *Exserohilum zeicola*) disease rating is scored visually on a scale of 1 to 9, with 9 indicating the highest disease resistance.

GLS (gray leaf spot; *Cercospora zeae*) disease rating is scored visually on a scale of 1 to 9, with 9 indicating the highest disease resistance.

ES (eye spot; *Kabatiella zeae*) disease rating is scored visually on a scale of 1 to 9, with 9 indicating the highest disease resistance.

SWILT (Stewart's wilt; *Erwinia stewartii*) disease rating is scored visually on a scale of 1 to 9, with 9 indicating the highest disease resistance.

Color Code

01—Light Green; 02—Medium Green; 03—Dark Green; 04—Very Dark Green; 05—Green-Yellow; 06—Pale Yellow;
07—Yellow; 08—Yellow-Orange; 09—Salmon; 10—Pink-Orange; 11—Pink; 12—Light Red;
13—Cherry Red; 14—Red; 15—Red & White;
16—Pale Purple; 17—Purple; 18—Colorless;
19—White; 20—White Capped; 21—Buff; 22—Tan;
23—Brown; 24—Bronze; 25—Variegated (Describe);
26—Other (Describe).

Stay Green is a visual rating of the color of the plant at 65 days after anthesis. The rating scale is from 1 to 9, with 1 being the worst stay green capacity (early die-back), and 9 being the best stay green capacity (late die-back).

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Features and advantages of the invention will be apparent from the following detailed description, and from the claims.

DETAILED DESCRIPTION

Seeds of the inbred corn line designated BE4547 were deposited on Nov. 9, 1998, in the American Type Culture Collection (ATCC), Manassas, Va. 20852 U.S.A. The ATCC Accession No. is 203444. The deposited seeds were from the deposit maintained by Cargill, Inc., Wayzata, Minn. since prior to the filing date of this application. The ATCC deposit of inbred line BE4547 will be maintained without restriction in the ATCC depository for a period of 30 years, or five years after the most recent request, or for the effective life of the patent, whichever is longer. The deposit will be replaced if it becomes non-viable during that period. In making the BE4547 deposit, applicants have satisfied all the requirements of 37 C.F.R. §§ 1.801–1.809.

Inbred corn line BE4547 is a yellow dent corn (maize) inbred that is useful as one parent to produce $F_1$ hybrid corn. BE4547 is particularly suited for use as the male parent to produce single cross $F_1$ hybrid seed corn. Inbred line BE4547 is adapted to the central corn belt of the United States. It can be used to produce hybrids from an average relative maturity of 100–110 days, based on the Comparative Relative Maturity Rating System for harvest moisture of grain. As an inbred per se, BE4547 is average yielding, with girthy ears of moderate length, and yellow dent kernels. It contributes rapid drydown and provides superior stalk and root characteristics, resulting in improved hybrid harvest moistures and standability. Hybrids involving BE4547 have high yields for maturity in high yield environments.

BE4547 shows uniformity and stability within the limits of environmental influence for the traits described in the data tables below. The BE4547 inbred line has been self-pollinated and ear-rowed for a sufficient number of generations to ensure sufficient homozygosity and phenotype stability for use in commercial production. BE4547 has been increased in appropriately isolated fields, under observation for uniformity, according to methods accepted in the corn seed industry. No significant variant traits have been observed in BE4547.

Inbred line BE4547 can be propagated by conventional plant breeding methods. BE4547 corn plants are grown to maturity under self-pollinating or sib-pollinating conditions with adequate isolation from corn plants of other genotypes. The resulting seeds are harvested and stored under conditions of suitable temperature and humidity.

In addition to propagation by conventional plant breeding methods, inbred corn line BE4547 can be maintained, manipulated, genetically transformed, or propagated by means of corn tissue culture. Techniques suitable for producing corn tissue cultures from inbred line BE4547, and regenerating fertile BE4547 corn plants from the tissue cultures are known in the art. Corn tissue culture techniques are described in numerous references, e.g., Hibberd et al., U.S. Pat. No. 4,581,847; Kamo et al., "Establishment and Characterization of Long-Term Embryogenic Maize Callus and Cell Suspension Cultures," Plant Science 45:111–117 (1986); Vasil et al., "Plant Regeneration from Friable Embryogenic Callus and Cell Suspension Culture of *Zea mays* L.," *J. Plant Physiol.* 124:399–408 (1986).

Inbred corn line BE4547 can be used as starting material for production of transgenic corn plants. Application of known methods for producing transgenic corn plants is within ordinary skill in the art. For an illustrative example of production of transgenic corn plants, see, e.g., U.S. Pat. No. 5,484,956. Examples of transgenes that can be introduced into corn line BE4547 include those conferring herbicide resistance, insect resistance, disease resistance, improved amino acid content of seed storage proteins, and improved nutritional quality of seed oil.

A substantially uniform assemblage of $F_1$ hybrid corn seed can be prepared using BE4547 as one parent. Such hybrid seeds can be conditioned and bagged in packaging material by means known in the art to form an article of manufacture. Such a bag of seed preferably has a package label accompanying the bag, e.g., a tag or label secured to the packaging material, a label printed on the packaging material or a label inserted within the bag. The package label indicates that the seeds therein are effective for producing corn grain.

Hybrid seed is purchased by growers, who then plant and cultivate the seed according to standard agronomic practices in the geographic area to which the hybrid is adapted. Growers will also typically take into account soil fertility, crop rotation practices and other factors specific to the locale in which the hybrid corn is being grown.

Inbred BE4547, and grain produced by employing inbred line BE4547, can be used as human food, livestock feed, and as raw material in industry. In addition to direct consumption of corn as food, corn-derived food products can be produced by industrial methods of dry-milling or wet-milling. Exemplary products of corn dry milling are grits, meal and flour. Exemplary products of wet-milling are corn starch, corn syrup, and dextrose for food use. Corn oil is obtained from corn germ, which is a by-product of both the dry- and wet-milling industries. Grain and non-grain portions of the corn plant, can be used as livestock feed, e.g., for beef cattle, dairy cattle, hogs, and poultry.

In addition to food uses, corn of the invention can be used in non-food, industrial applications. For example, grain can be used to produce corn starch or corn flour for non-food, industrial applications. These applications depend on functional properties, such as viscosity, film formation, adhesive properties, and ability to suspend particles. Corn starch and corn flour are useful, e.g., in the paper industry and textile industry. Corn of the invention also can be used industrially in adhesives, building materials, foundry binders, laundry starches, explosives, oil-well muds, and other mining applications. In addition to grain, other BE4547 corn plant parts are useful in industry. Stalks and husks can be processed into paper or wallboard. Cobs can be used for fuel or to make charcoal.

The characteristics of inbred maize line BE4547 are summarized and compared in Table 1 below to characteristics of a reference inbred designated herein as IB706.

TABLE 1

Summary of BE4547 Characteristics

| Parameter | BE4547 Average ± Std.Dev. (n = 20) | IB706 Average ± Std. Dev. (n = 20) |
|---|---|---|
| Maturity - Silk (days) (GDU) | (90) (1425) | (96) (1527) |
| Maturity - pollen (days) (GDU) | (88) (1367) | (94) (1479) |
| Plant Height (cm) | 167.6 ± 11.89 | 204.4 ± 9.28 |
| Ear Height (cm) | 45.6 ± 8.99 | 65.4 ± 8.80 |
| Length of Top Ear (cm) | 12.6 ± 0.92 | 14.4 ± 2.07 |
| Avg # Ears | 1.0 | 1.0 |
| Anthocyanin - brace roots | 3 | 2 |
| Width Ear Node Leaf (cm) | 8.0 ± 0.70 | 10.6 ± 0.79 |
| Length Ear Node Leaf (cm) | 83.0 ± 3.39 | 71.3 ± 2.53 |
| No. Lvs Above Ear | 4.9 ± 0.57 | 5.0 |
| Degrees Leaf Angle | 25.8 ± 3.63 | 29.8 ± 4.60 |
| Leaf Color | 02 | 25 |
| Leaf Sheath Pubesc. | 3 | 2 |
| Leaf Margin Waves | 5 | 5 |
| Longitudinal Waves | 1 | 1 |
| No. Prim. Lat. Branches | 7.2 ± 1.54 | 3.2 ± 0.73 |
| Branch Angle | 22.5 ± 5.36 | 30.0 ± 17.60 |
| Tassel Length (cm) | 44.2 ± 2.01 | 47.6 ± 2.46 |
| Pollen Shed | 6 | 5 |
| Anther Color | 17 | 07 |
| Glume Color | 02 | 03 |
| Bar Glumes | 1 | 1 |
| Silk Color | 07 | 07 |
| Fresh Husk Color | 02 | 05 |
| Dry Husk Color | 02 | 05 |
| Position of Ear at Dry Husk Stage | 3 | 1 |
| Husk Tightness | 6 | 7 |
| Husk Extension | 2 | 2 |
| Ear Length (cm) | 13.9 ± 1.37 | 14.1 ± 1.72 |
| Mid Point Diam (mm) | 41.4 ± 2.96 | 35.0 ± 2.16 |
| Ear Weight (gm) | 60.9 ± 21.25 | 61.6 ± 18.53 |
| Number of Kernel Rows | 15.4 ± 2.01 | 10.9 ± 0.99 |
| Kernel Rows | 2 | 2 |
| Row Alignment | 1 | 2 |
| Ear Taper | 1 | 1 |
| Kernel Length (mm) | 9.5 ± 0.87 | 10.2 ± 0.65 |
| Kernel Width (mm) | 7.4 ± 0.92 | 8.6 ± 0.59 |
| Kernel Thickness (mm) | 5.0 ± 0.63 | 5.1 ± 0.77 |
| % Round Kernels | 80.1 ± 18.21 | 80.4 ± 11.27 |
| Aleurone Color Pattern | 1 | 1 |

TABLE 1-continued

Summary of BE4547 Characteristics

| Parameter | BE4547 Average ± Std.Dev. (n = 20) | IB706 Average ± Std. Dev. (n = 20) |
|---|---|---|
| Aleurone Color | 07 | 07 |
| Hard Endosperm Color | 19 | 19 |
| Endosperm Type | 3 | 3 |
| 100K wt. (gm) | 23.6 ± 5.01 | 30.0 ± 3.15 |
| Mid Cob Diam. (mm) | 27.9 ± 1.95 | 18.8 ± 1.61 |
| Cob Color | 19 | 12 |
| Stay Green | 1 | 1 |
| % Dropped Ears | 20.0 | 0.0 |
| % Root Lodging | 75.0 | 30.0 |
| Yield Per Se (kg/ha) | 1417.9 | 1568.0 |

BE4547 is shorter in plant height and ear height than IB706. Anthocyanin in the brace roots is somewhat more distinct in BE4547 than in IB706. BE4547 matures to 50% silk and 50% pollen significantly earlier than IB706. BE4547 has a narrower, but longer, ear node leaf, as compared to that of IB706. BE4547 leaf color does not include the lighter green spots found on IB706. The tassel of BE4547 has a significantly greater number of primary lateral branches, and the branches are more erect. The tassel of BE4547 is slighter shorter in length than the tassel of IB706. The anthers of BE4547 are distinguished by their purple color, as compared to the yellow anthers of IB706. The glumes of BE4547 display a slighter lighter green color than the glumes of IB706.

The silk colors of BE4547 and IB706 are a comparable yellow color. Both the fresh and dry husks of BE4547 are more green in color, as compared to the green-yellow husks of IB706. At the dry husk stage, the ear of BE4547 tends to hang downward (pendant position), while the ear of IB706 remains relatively more upright. The husked ear diameter of BE4547 is larger than that of IB706, and it has a significantly greater number of kernel rows. Ear weights and lengths are similar for the two inbreds. The cob diameter at the midpoint for BE4547 is much larger than that for IB706. The cob of BE4547 is white, in contrast to the light red cob of IB706. Kernel length, width, and thickness are slightly smaller for BE4547. The percentage of round kernels is very similar for the two inbreds, as is aleurone color and endosperm color. The 100 kernel weight of BE4547 is smaller than that of IB706.

TABLE 2

BE4547 Disease Resistance

| NLB | SLB | NLS | GLS | ES | SWILT |
|---|---|---|---|---|---|
| 5 | 5 | 6 | 5 | 7 | 4 |

Table 2 summarizes the disease resistance scores compiled from observations during the 1996–1998 seasons. Disease resistance is above average for eyespot and northern leaf spot. BE4547 is moderately susceptible to northern leaf blight, southern leaf blight, grey leaf spot, and Stewart's wilt. Hybrid disease resistance in hybrids having BE4547 as a parent is enhanced by resistances contributed by the other parent of the hybrid.

TABLE 3

Hybrid Performance Data

| Hybrid | Reps | Yield bu/ac | % Moist | % Stalk | % Root | Test Wt. |
|---|---|---|---|---|---|---|
| 1131204 | 1080 | 158.45 | 19.35 | 4.85 | 0.63 | 57.08 |
| HC632 | | 151.57 | 19.69 | 4.44 | 1.27 | 57.94 |
| 1131204 | 807 | 156.81 | 18.44 | 4.54 | 1.01 | 57.50 |
| HW889 | | 153.10 | 17.23 | 5.23 | 1.33 | 57.35 |
| 1131204 | 582 | 155.22 | 19.99 | 5.53 | 0.40 | 57.31 |
| HM896 | | 141.15 | 20.01 | 5.17 | 1.62 | 57.29 |
| 1131204 | 384 | 162.63 | 19.44 | 5.13 | 0.88 | 56.83 |
| HY154 | | 146.35 | 19.14 | 2.80 | 3.01 | 56.71 |

Table 3 contains hybrid performance data comparing single cross hybrid 1131204 with several commercial hybrids. The male parent of 1131204 is BE4547. In comparison with a hybrid designated HC632, 1131204 has a yield advantage, is slightly drier, has similar stalk lodging, less root lodging, and lighter test weight. When tested against a hybrid designated HW889, hybrid 1131204 was higher yielding, over 1% wetter, had less stalk lodging, less root lodging, and similar test weight. The comparison with a hybrid designated HM896 showed a significant yield advantage for 1131204, similar moisture and stalk lodging, less root lodging, and essentially equal test weights. In a comparison with a hybrid designated HY154, hybrid 1131204 was significantly higher yielding, was slightly higher in moisture, had greater stalk lodging, but much less root lodging, and similar test weight.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An inbred corn seed designated BE4547, represented by BE4547 seed deposited as ATCC accession number 203444.

2. A corn plant produced from the seed of claim 1.

3. A plant part of the plant of claim 2.

4. A pollen grain of the plant of claim 2.

5. A tissue culture derived from the corn plant of claim 2 or plant part of claim 3.

6. An $F_1$ hybrid corn seed produced by crossing a first corn inbred plant designated BE4547, represented by BE4547 seed deposited as ATCC Accession No. 203444, with a second inbred plant.

7. A corn plant grown from the $F_1$ hybrid corn seed of claim 6.

* * * * *